United States Patent [19]

Cooper

[11] Patent Number: 5,045,708
[45] Date of Patent: Sep. 3, 1991

[54] RADIATION SHIELD FOR PROTECTING INTERNAL BODY ORGANS

[76] Inventor: William I. Cooper, 300 N. Fourteenth St., Easton, Pa. 18042

[21] Appl. No.: 567,799

[22] Filed: Aug. 15, 1990

[51] Int. Cl.⁵ ............................................. G21F 3/02
[52] U.S. Cl. ............................. 250/519.1; 250/515.1; 250/516.1; 250/517.1
[58] Field of Search ............... 250/519.1, 517.1, 515.1, 250/505.1, 516.1; 128/653 R, 659; 600/1, 3

[56] References Cited

U.S. PATENT DOCUMENTS

| | | | |
|---|---|---|---|
| 3,025,403 | 3/1962 | Belknap et al. | 250/519.1 |
| 3,185,751 | 5/1965 | Sutton | 250/519.1 |
| 3,310,053 | 3/1967 | Greenwood | 250/519.1 |
| 3,569,713 | 3/1971 | Via, Jr. | 250/519.1 |
| 3,696,810 | 10/1972 | Gaylord, Jr. | 128/75 |
| 3,845,316 | 10/1974 | Tureck | 250/519.1 |
| 4,024,405 | 5/1977 | Szot | 250/519.1 |
| 4,074,397 | 2/1978 | Rosin | 24/73 |
| 4,220,867 | 9/1980 | Bloch, Jr. | 250/519.1 |
| 4,223,229 | 9/1980 | Persico et al. | 250/515.1 |
| 4,313,437 | 2/1982 | Martin | 128/207.17 |
| 4,672,722 | 6/1987 | Malamed | 24/446 |
| 4,907,717 | 3/1990 | Kubojcik | 250/519.1 |

Primary Examiner—Jack I. Berman
Assistant Examiner—Kiet T. Nguyen
Attorney, Agent, or Firm—Pollock, Vande Sande & Priddy

[57] ABSTRACT

A radiopaque shield for protecting internal body organs when a nearby body member is being irradiated by X-rays in diagnostic or therapeutic procedures. The shield is a flexible radiopaque pouch configured to fit over the body part to be protected.

8 Claims, 1 Drawing Sheet

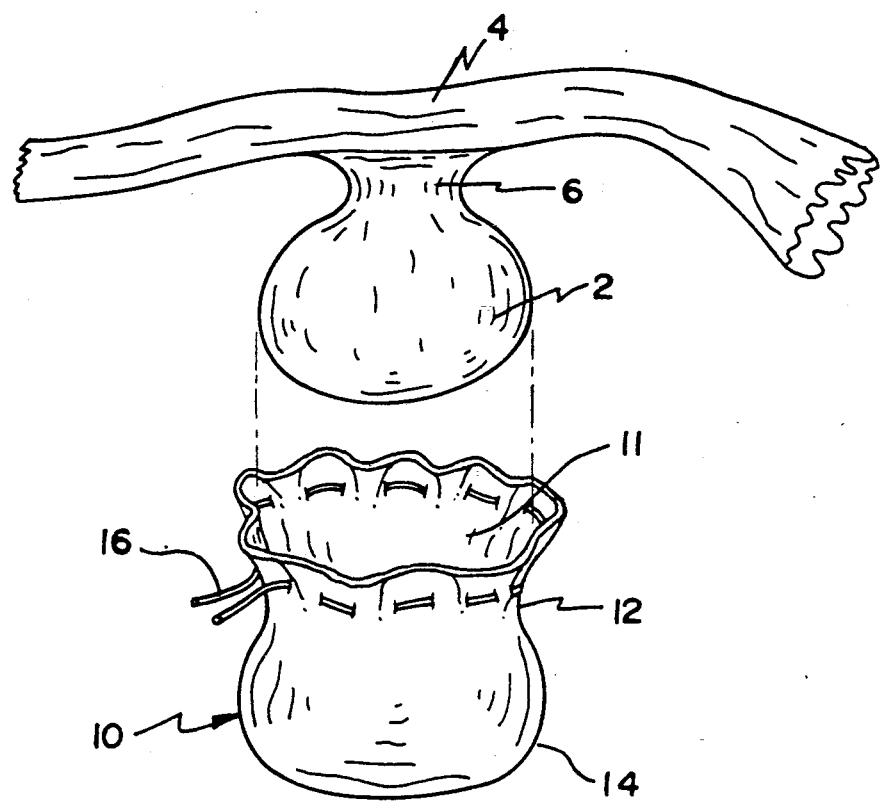
FIG. 1
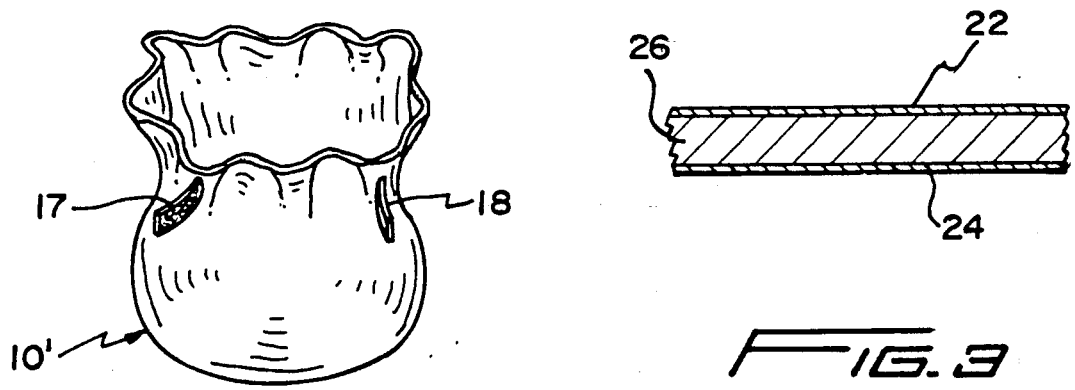
FIG. 2
FIG. 3

RADIATION SHIELD FOR PROTECTING INTERNAL BODY ORGANS

This invention relates to devices for shielding the human body against radiation, and more specifically to shielding devices for protecting specific internal body organs from radiation during diagnostic or therapeutic procedures using X-rays.

BACKGROUND OF THE INVENTION

The strong biological effects of X-rays on the human body and the dangers associated therewith require the use of X-ray shielding devices when using X-rays in diagnostic and therapeutical procedures. The shielding devices are intended to limit the radiation exposure to the specific portions of the body which must be exposed to achieve the desired purpose. In order to limit the exposure to radiation, shields of various configurations have been placed between a patient and an X-ray source. See, for example, U.S. Pat. Nos. 3,569,713 to Via, Jr.; 4,024,405 to Szot; 4,220,867 to Bloch, Jr.; and, 4,223,229 to Persico et al.

U.S. Pat. No. 3,569,713 to Via, Jr. discloses an X-ray shield to protect the thyroid gland of a dental patient. The protector is in the form of a shield which covers the forward portion of the neck over and above the larynx.

U.S. Pat. No. 4,024,405 to Szot describes a shield for protecting a patient's eyes during exposure to medial and dental X-rays.

U.S. Pat. No. 4,220,869 to Bloch, Jr. discloses a protective shield for the neck, which includes a lead sheet secured within a synthetic form pad member which is covered with a cloth.

U.S. Pat. No. 4,223,229 to Persico et al describes a shield for protecting the teeth and related body areas during radiation.

The shields described in the cited patents are placed between the patient and the X-ray source and thus restrict the area which is exposed to radiation to an uncovered portion of the patient's body. However, a shield which is external to the patient's body is relatively ineffective in pinpointing the zone to be irradiated when the organ to be treated is near a zone to be protected and the two zones are relatively small, are close together and are located deep within the body. For example, there is a need to protect a woman's ovaries and thus her reproductive capacity (or at least the hormonal function of the ovaries) during pelvic radiation. However, typically a shield placed outside the body for protecting the ovaries while the pelvic region is being irradiated is not sufficiently selective in its shielding function.

SUMMARY OF THE INVENTION

It is one object of the present invention to provide an improved radiation shield for protecting internal body organs from radiation when using X-rays in diagnostic or therapeutic procedures.

In accordance with the present invention, there is provided a radiation shield for selectively protecting an internal body organ during radiation of a nearby body member. The shield is a flexible, radiopaque pouch configured for fitting over an internal body organ for reducing the exposure of the organ to radiation. Means are provided for securing the pouch in place on the body organ.

The radiation shield of the present invention is capable of selectively shielding a body organ even when the target for radiation is adjacent to the shielded organ. Further, the shield is effective in reducing the radiation which strikes the shielded organ, regardless of the direction from which the radiation is emitted.

BRIEF DESCRIPTION OF THE DRAWINGS

FIG. 1 is an exploded view of one embodiment of the present invention showing a specific application of a shield to a body organ.

FIG. 2 is a view of an embodiment of the present invention showing an alternative means for retaining the shield in place on a body organ.

FIG. 3 is a representative section through the wall of one embodiment of the present invention.

DETAILED DESCRIPTION OF THE INVENTION

The shield of the present invention is especially useful in protecting a woman's ovaries during radiation of the pelvic region, and the present invention will be described in detail in its application to protection of the ovaries. However, it should be understood that the present invention is not restricted to such use, but may be adapted for protecting other internal body organs.

Referring now in detail to the drawings, FIG. 1 depicts an ovary 2 joined to fallopian tube 4 by ovarian ligament 6. The ovary is to be protected during radiation of the pelvic region by pouch 10 comprising a flexible radiopaque material which is described in more detail below. As shown in Figure 1, drawstring 16 is provided to hold the pouch in place during radiation.

In another embodiment of the shield of the present invention, as shown in FIG. 2, pouch 10' is provided with tabs 17, 18 having surfaces which are capable of adherence to and separation from one another. Typically useful tabs are those having a pressure-sensitive adhesive on a mating surface of at least one tab, or having an area carrying a Velcro fastener.

Other suitable means for retaining the shield in place during radiation include an elastic strip as part of the pouch at neck zone 12 near opening 11 of the shield. The pouch could also be held in place by suturing it to an ovary.

The pouch may be formed from a flexible, radiopaque material, such as, for example, a flexible sheet containing particles of a heavy metal. The sheet is preferably formed from an elastomer such as natural rubber, or one of the synthetic resins such as the methacrylates, or the synthetic polyamides, such as nylon. The heavy metal which is incorporated into the sheet may be any of the heavy metals such as iron, and is preferably lead.

In a preferred embodiment of the present invention, as shown in FIG. 3, the shield is a laminate of three layers 22, 24, 26 of a film-like material, the intermediate layer 26 containing lead and the outer layers 22, 24 being lead-free in order to prevent lead particles from contacting the human body.

In one embodiment of the present invention, the wall of the neck portion 12 of pouch 10 is thinner than the wall in the body portion 14 to provide sufficient flexibility to permit neck portion 12 to be tightened in use. A flexible neck portion may be achieved by eliminating the intermediate lead-bearing layers from the neck portion of a three layer pouch.

Methods of making flexible radiopaque articles comprising heavy metals in an elastomeric sheet are well-known in the art as exemplified by U.S. Pat. No. 3,025,403 to Belknap et al, and U.S. Pat. No. 3,185,751 to Sutton. Each of these patents describes a method of incorporating lead particles in elastomeric material. For example, U.S. Pat. No. 3,185,751 to Sutton describes a rubber glove containing lead having an average particle size of 2 microns in an amount 5 times the weight of the rubber. The teachings of these patents concerning the methods of incorporating lead in flexible materials are hereby incorporated by reference.

The walls of the flexible radiopaque pouch may be from about 2 to about 5 mils, and can be made in thicknesses at least as great as 50 mils, while still retaining adequate flexibility for use in protecting ovaries. As noted above, in a preferred embodiment of the present invention, the lead containing elastomeric layer is covered on each side with a lead-free elastomeric layer, each of which may be, for example, 2-5 mils thick, for preventing contamination by lead.

The shield of the present device may be placed and removed by methods well-known to workers in the art such as by laparoscopic surgery.

The foregoing is intended to illustrate and not to restrict the scope of the present invention, which should be limited only as indicated by the following claims.

What is claimed is:

1. A radiation shield for protecting an internal body organ during radiation of a nearby body member, said shield comprising:

a flexible radiopaque pouch having an open end and a closed end and configured for fitting over said body organ to enclose at least a portion thereof; and, means for securing said radiopaque pouch on said body organ.

2. A radiation shield according to claim 1 wherein said pouch is configured to enclose at least a portion of a woman's ovary.

3. A radiation shield according to claim 1 wherein said means for securing said pouch on said body organ comprises elastic means at said open end of said pouch.

4. A radiation shield according to claim 1 wherein said means for securing said pouch on said body organ comprises a drawstring for tightening said open end about said body organ.

5. A radiation shield according to claim 1 wherein said pouch comprises a flexible sheet containing particles of a heavy metal.

6. A radiation shield according to claim 5 wherein said flexible sheet comprises an elastomeric material and said heavy metal is lead.

7. A radiation shield according to claim 5 wherein said flexible sheet comprises an inner heavy metal-free film, an outer heavy metal-free film and an intermediate film, said intermediate film containing particles of a heavy metal.

8. A radiation shield according to claim wherein the portion of said pouch near said open end is more flexible than the portion of said pouch near said closed end.

* * * * *